United States Patent [19]

Bentsen

[11] 4,134,771

[45] Jan. 16, 1979

[54] IMPREGNATING LIQUID FOR WOOD AND WOOD PRODUCTS

[75] Inventor: Aksel T. Bentsen, Kolding, Denmark

[73] Assignee: Gorivaerk AS, Kolding, Denmark

[21] Appl. No.: 812,064

[22] Filed: Jul. 1, 1977

[30] Foreign Application Priority Data

Jul. 5, 1976 [DK] Denmark .............................. 3032/76

[51] Int. Cl.² .......................... C08K 5/29; C09D 5/14
[52] U.S. Cl. .......................... 106/15 R; 260/45.75 T; 260/45.9 KA; 424/288
[58] Field of Search ..................... 260/23.7 A, 23.7 R, 260/97.5, 414, 429.7, 19 N, 23.3, 23.7 M, 45.7 ST, 45.9 KA; 106/15; 424/288

[56] References Cited

U.S. PATENT DOCUMENTS

| | | | |
|---|---|---|---|
| 2,970,923 | 2/1961 | Sparmann | 106/15 AF |
| 3,214,453 | 10/1965 | Stern | 260/45.75 K |
| 3,400,201 | 9/1968 | Mocotte | 106/15 AF |

*Primary Examiner*—Ronald W. Griffin
*Attorney, Agent, or Firm*—Fleit & Jacobson

[57] ABSTRACT

Impregnating liquid for wood and wood products containing a reaction product between tributyl tin oxide and one or more naphthenic acids and a non-oxidative drying binder comprising a polydiene resin. Said impregnating liquid can further comprise 2,4,5,6-tetrachlorisophthalonitrile.

5 Claims, No Drawings

IMPREGNATING LIQUID FOR WOOD AND WOOD PRODUCTS

The present invention relates to an impregnating liquid for wood and wood products and of the type containing a fungicidally active organo-tin compound and a binder dissolved in an organic solvent. Said liquid is particularly suitable for vacuum impregnation, but may also be used in other forms of impregnation, such as immersion or application.

A very widespread fungicide, also for use in wood impregnating liquids, is bis-(tributyl tin)oxide (TBTO), cf. for example British Pat. Nos. 1,059,629 and 1,419,373, Danish published application No. 133,336 and Danish patent application No. 1703/75. The use of TBTO, however, as also emphasized in published application No. 133,336 involves certain disadvantages, for instance the unpleasant smell of the compound which is conditioned by its high vapor pressure, and its low washing- and UV-stability and resultant occasionally insufficient effectivity.

It has also been found that certain persons are allergic to the substance so that there is produced contact allergy phenomena which may cause skin irritations, just as the substance may cause headaches after using it for a shorter or longer period of time.

One or more binders also enter into current impregnating compositions on a solvent base, such as vacuum impregnation compositions, and these binders have, in principle, three functions:

(1) Fixation of the biocide so that the washing is reduced or eliminated.

(2) Improved adhesion of the compositions applied during subsequent treatment, in other words a primer effect.

(3) Reduction of the water vapor permeability by stopping up the pores. In this way the surface is also rendered water repellent and the wood is dimension-stabilized against future moisture action.

Two different types of binder may be used, viz. the oxidative drying and the non-oxidative drying binders.

Oxidative drying binders used are, among others, for example low molecular alkyds, partly polymerized esters of glycerol or pentaerythritol and unsaturated carboxylic acids, such as tall oil fatty acids, as well as cyclopentadiene adducts to various oils.

The non-oxidative drying binders are for instance various polymers, such as so-called petroleum resin which is a polydiene resin, cumarone-indene resins, ketone resins, such as polycyclohexanone resins which may possibly be phenol-modified, as well as aldehyde resins, such as aromatic formaldehyde resins.

Impregnating liquids on the basis of TBTO usually contain major or minor amounts of an oxidative drying binder. This may reduce the drawbacks involved in using TBTO, but unfortunately also reduces the fungicidal activity of TBTO, especially when used in high concentrations to fulfil the above-mentioned objects. The reduction at high concentrations is particularly due to an encapsulation of the TBTO molecules which is significant already at binder concentrations of about 7.5%. The additional drawback is added that the storing stability when using oxidative drying binder is low where the oxygen of air may have unimpeded admission to the liquid for long periods of time, which is the case for instance in vacuum impregnation plants. Said disadvantage can be reduced but not entirely eliminated by continual dosing of anti-oxidants to the liquid in the stockpile.

It has also been attempted to combine TBTO with non-oxidative drying binders. Normally, these do not noticeably reduce the fungicidal activity, but on the other hand they do not reduce the drawbacks involved in using TBTO either. On the contrary, it has been found in practice that they add a further disadvantage, causing in some cases poorer adhesion of the compositions subsequently applied, in other words a reduced primer effect. These drawbacks are so decisive that in practice TBTO is predominantly used in combination with oxidative drying binders.

Danish patent application No. 5279/67 describes fungicidally active compounds of the general formula:

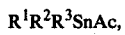

$$R^1R^2R^3SnAc,$$

in which $R^1$, $R^2$ and $R^3$ designate identical or different alkyl or aryl groups and Ac designates the residual acid of a fatty acid, the only concretely mentioned compound, however, being triphenyl tin stearate. Thus, tributyl compounds are not mentioned, but are, however, formally comprised by the above-mentioned formula. It is stated that the fatty acid derivatives described have no local irritation effect, but their fungicidal activity and the stability thereof has not been substantiated. Nor has the compatibility with various types of binder been mentioned or examined, and the forms of application mentioned comprise only pure solutions without addition of binder.

Although, perphaps, it might thus be assumed that by reacting TBTO with a fatty acid the fungicidal activity might be retained and the inconveniences to be ascribed to the irritating character of TBTO eliminated, it must be regarded as surprising that by reacting TBTO with one or more long chain carboxylic acids it was possible to eliminate also the other disadvantages and besides to obtain a product exhibiting excellent compatibility with non-oxidative drying binders in impregnating liquids for wood or wood products, particularly for vacuum impregnation, just as an extremely good adhesion of subsequently applied paints is observed after impregnation.

The impregnation liquid according to the invention is therefore characteristic in that it contains a reaction product between tributyl tin oxide and one or more long chain carboxylic acids as well non-oxidative drying binder.

The preferred long chain carboxylic acids are naphthenic acids, partly because they are very inexpensive, and partly because they have turned out in practice to yield the best results. However, it is also possible to use for example tall oil fatty acids having at least 12 carbon atoms.

Said reaction products may be combined with non-oxidative drying binders of the kind described above and an organic solvent, such as white spirit, to obtain an impregnating liquid that is well-suited for vacuum impregnation of wood. The product has extremely good storing stability, has good penetration, and affords an effective and durable protection, as it is very stable against washing and ultraviolet light, just as it provides surprisingly good adhesion of the subsequently applied surface treatment systems.

The preferred binder is the commercially available so-called petroleum resin which is a polymerization product of an unsaturated $C_5$ fraction from steam cracking of naphtha and having an average molecular weight of about 1500, as this type of resin combines extremely satisfactory solubility and stability properties with a reasonable price. Such polydiene resins are sold for instance under the trade names "Escorez 1102B" and "Imprez 100".

An impregnating liquid according to the invention for vacuum impregnation of wood may suitably contain from ½ to 5 percent by weight of reaction product between TBTO and carboxylic acid and from 2 to 20 percent by weight of non-oxidative drying binder dissolved in an organic solvent, such as white spirit, said combination providing the most balanced penetration and dimension stability.

A particularly suitable combination is 2 percent by weight of tributyl tin naphthenate and 5 percent by weight of polydiene resin, said combination providing by normal impregnating practice a satisfactory protective effect in accordance with the existing rules of approval.

Other protectants may also be added, such as UV-absorbing agents, particularly hydrophobically active surfactants, compositions against surface mould, penetration-promoting agents and dyes.

These various protectants may be used to supplement the fungicidal activity of TBTN so as to obtain the most suitable spectrum of protection in consideration of the expected loadings of the impregnated product, but as a principal rule there is not obtained a protection surpassing that which might be expected from the proterties of the compositions concerned.

It has suprisingly been found, however, that a composition against surface mould known per se, viz. 2,4,5,6-tetrachlorisophthalonitrile, displays a synergy action with the constituent fungicide, represented by TBTN, the obtained wood protection surpassing by far the expected additive effect of the individual components, as documented below.

By means of the compositions according to the invention the disadvantages known from TBTO are completely eliminated:

The reaction product used according to the invention, in the following named TBTN, is almost odourless, and no case of headaches has been reported as a result of using the composition.

The skin-irritating effect of the composition has also been examined in TBTO-sensitive persons, and it does not exceed the effect of a blind test with white spirit.

The fungicidal activity has been examined by means of the so-called sobeto test where wooden blocks were impregnated with the test compound and put into the soil for 5 weeks were exposed to a test fungus (Coniophora cerebella) with and without intermediate washing treatment, respectively. Hereafter the loss of substance in percent was determined, untreated blocks being used as control.

The results will appear from the below table where reaction products of 50% TBTO and 50% naphthenic acid, reacted at 120° C., were used as active substance.

| TBTN, calculated as % TBTO | Intermediate Washing | Loss of Substance % | |
|---|---|---|---|
| | | Treated | Untreated |
| 0.6 | + | 0.04 | 25 |
| 0.6 | − | 0.56 | 28 |
| 0.8 | + | 0.29 | 26 |
| 0.8 | − | 0.58 | 25 |
| 1.0 | + | 0 | 23 |
| 1.0 | − | 0.52 | 18 |
| 1.2 | + | 0.89 | 27 |

-continued

| TBTN, calculated as % TBTO | Intermediate Washing | Loss of Substance % | |
|---|---|---|---|
| | | Treated | Untreated |
| 1.2 | − | 1.8 | 26 |

The prescriptions used were as follows:

| TBTO | 0.6% | 0.8% | 1% | 1.2% |
|---|---|---|---|---|
| Reaction product | 1.2% | 1.6% | 2.0% | 2.4% |
| Polydiene resin | 9.5% | 12.0% | 15.0% | 18.0% |
| Solvent (white spirit) | 89.8% | 86.4% | 83.0% | 79.6% |

In this standard test the maximum loss of substance permissible is 3%, and it will thus be seen that the examined concentrations are all satisfactory.

By way of comparison it is stated that the lower limit to unreacted TBTO in this test is 0.75%, which shows that improved fungicidal activity is achieved by using TBTN.

Finally, experiments have been made as to the influence of the various impregnating compositions on the adhesion of various paint systems on an oil base, alkyd base, acryl base, and polyurethane base, respectively, on planed pinewood panels of the dimensions 200 × 100 × 16 mm.

The panels were immersed in the impregnating liquid for 1–2 minutes and 24 hours after the impregnation 4 different paint systems were applied in 2 layers at 24 hours' interval between application of the individual layers.

The degree of adhesion was determined according to SIS 184 171 "tensile test" with tensile test specimen of an area of 3,14 $cm^2$ to which had been glued a solvent-free epoxy two-component adhesive. The results stated below are mean values of the 4 different paint systems, for each of which 3 tensile test determinations were made.

| | (Tensile Force per unit area) Tensile Force |
|---|---|
| 1.1% of TBTO + 7.2% of oxidative drying binder | 2.82 MPa |
| 1.25% of TBTO + 7.5% of non-oxidative drying binder (polydiene resin) | 3.05 MPa |
| 1.0% of TBTO as 2% of TBTN + 7.5% of non-oxidative drying binder | 3.17 MPa |

It will hence be seen that the best adhesion is achieved by the combination of TBTN and non-oxidative drying binder. Even in case of longer drying times and after a 1-year weathering test (outdoor exposure 45° towards the south) this combination is judged to be fully up to the standard of TBTO in combination with oxidative drying binder as regards primer effect.

FUNGICIDAL ACTIVITY IN SOIL CONTACT

The fungicidal activity in soil contact has been examined by the so-called Mullada test (Nordic Wood Preservation Committee, standard (NWPC) 1412/70 "Testing against surface rot". In said test 2 × 10 × 70 mm beech sticks, impregnated with the test composition in a quantity of 150 kg/$m^3$ were placed in soil for 6 weeks. Untreated control sticks were used in comparison, and tests were carried through with and without an intermediate washing treatment. The loss of substance attained after the test period is a measure of the efficiency of the compositions.

It is pointed out that this test feigns very hard conditions for vacuum impregnated wood, as it is normally advised not to use such wood in direct soil contact precisely on account of the risk of decomposition owing to surface rot and surface mould. Still, it is of course an advantage that the wood exhibits the best possible resistancy in this test, and this also indicates an even exceptionally good resistancy when used out of soil contact.

In the present case an examination has been made partly of an impregnating liquid according to the invention containing 2 percent by weight of TBTN in combination with 5% of a non-oxidative drying binder ("Escorez 1102 B"), partly, in comparison, an impregnating liquid containing only 1½% of 2,4,5,6-tetrachlorisophthalonitrile in combination with "Escorez 1102 B", and finally of an impregnating liquid according to the invention containing 1.8% of TBTN and 0.2% of tetrachlorisophthalonitrile (TCIPN).

The following results were obtained:

| Active Substance | Intermediate Washing | Loss of Substance % Treated | Loss of Substance % Untreated |
|---|---|---|---|
| 2% of TBTN + 5% of Escorez | + | 10.5 | 18.5 |
| " | − | 10.2 | 18.6 |
| 1.5% of tetrachlorisophthalonitrile + 5% of Escorez | + | 8.6 | 16.2 |
| " | − | 9.6 | 15.3 |
| 1.8% of TBTN + 0.2% of TCIPN + 5% of Escorez | + | 1.4 | 14.6 |
| " | − | 0.2 | 14.1 |

It will be seen that the composition according to the invention containing a combination of TBTN and tetrachlorisophthalonitrile shows a surprisingly low loss of substance compared to the loss of substance when using the individual constituents. Test with larger amounts of nitrile have produced no significantly improved effect.

What I claim is:

1. Impregnating liquid for wood and wood products based on an organic solvent containing a fugicidally active organo-tin compound and a binder, especially for use in vacuum impregnation, wherein the impregnating liquid contains a reaction product between tributyl tin oxide and one or more naphthenic acids and a non-oxidative drying binder comprising a polydiene resin which is a polymerization product of an unsaturated $C_5$ fraction from steam cracking or naphtha having an average molecular weight of about 1500.

2. The impregnating liquid in accordance with claim 1 and further comprising from ½ to 5 percent by weight of said reaction product between tributyl tin oxide and said naphthenic acids and from 2 to 20 percent by weight of said non-oxidative drying binder.

3. The impregnating liquid in accordance with claim 1 and comprising 2 percent by weight of tributyl tin naphthenate and 5 percent by weight of said polydiene resin.

4. The impregnating liquid in accordance with claim 1 and further comprising 2,4,5,6-tetrachlorisophthalonitrile.

5. The impregnating liquid in accordance with claim 4 and comprising 0.2 percent by weight of said 2,4,5,6-tetrachlorisophthalonitrile.

* * * * *